(12) United States Patent
Hopf

(10) Patent No.: US 7,767,712 B2
(45) Date of Patent: Aug. 3, 2010

(54) STORAGE-STABLE AQUEOUS COMPOSITION COMPRISING A MAGNESIUM COMPOUND AND L-CARNITINE

(75) Inventor: Günter Hopf, Tutzing (DE)

(73) Assignee: Verla-Pharm Arzneimittelfabrik Apotheker H.J.v. Ehrlich GmbH & Co. KG, Tutzing (DE)

( * ) Notice: Subject to any disclaimer, the term of this patent is extended or adjusted under 35 U.S.C. 154(b) by 120 days.

(21) Appl. No.: 11/743,683

(22) Filed: May 3, 2007

(65) Prior Publication Data

US 2007/0265339 A1 Nov. 15, 2007

(30) Foreign Application Priority Data

May 12, 2006 (EP) .................. 06009865

(51) Int. Cl.
*A61K 31/205* (2006.01)
*A61K 31/195* (2006.01)

(52) U.S. Cl. .................. 514/554; 514/566; 426/590; 426/594; 426/72; 426/73

(58) Field of Classification Search .............. 514/554, 514/566; 426/590, 594, 72, 73
See application file for complete search history.

(56) References Cited

U.S. PATENT DOCUMENTS

| 4,954,349 | A | * | 9/1990 | Sheth et al. | 424/461 |
| 5,071,874 | A | | 12/1991 | Scholl et al. | |
| 7,115,297 | B2 | * | 10/2006 | Stillman | 426/590 |
| 2002/0132219 | A1 | | 9/2002 | McCleary | |
| 2005/0002992 | A1 | * | 1/2005 | McCleary et al. | 424/439 |
| 2005/0053673 | A1 | | 3/2005 | Netke et al. | |
| 2005/0084551 | A1 | * | 4/2005 | Jensen et al. | 424/769 |
| 2005/0176144 | A1 | | 8/2005 | O'Daly | |

FOREIGN PATENT DOCUMENTS

| EP | 0680945 | 11/1995 |
| EP | 1163904 | 12/2001 |
| WO | 01/52647 | 7/2001 |
| WO | 0191759 | 12/2001 |

\* cited by examiner

*Primary Examiner*—Ardin Marschel
*Assistant Examiner*—Zohreh Vakili
(74) *Attorney, Agent, or Firm*—Renner, Otto, Boisselle & Sklar, LLP

(57) ABSTRACT

The present invention relates to a storage-stable aqueous or gel-like composition or solution comprising a magnesium compound selected from a magnesium salt or a magnesium complex compound, and L-carnitine, and the use thereof for the preparation of a medicament for supporting metabolism, in particular in muscle tissue, and for supporting muscle structure, and its use as food supplement or in the veterinary sector as animal feed additive, in particular for horses, poultry, pigeons, pigs, cattle, sheep and camels.

10 Claims, No Drawings

STORAGE-STABLE AQUEOUS COMPOSITION COMPRISING A MAGNESIUM COMPOUND AND L-CARNITINE

The present invention relates to a storage-stable aqueous or gel-like composition or solution comprising a magnesium compound selected from a magnesium salt or a magnesium complex compound, and L-carnitine, and the use thereof for the preparation of a medicament for supporting metabolism, in particular in muscle tissue, and for supporting muscle structure, and its use as food supplement or in the veterinary sector as animal feed additive, in particular for horses, poultry, pigeons, pigs, cattle, sheep and camels.

In the prior art, aqueous magnesium-containing solutions (for example Nupafeed®, marketed by Verla-Pharm) are known which contain approximately 50% by weight magnesium aspartate hydrochloride. This and higher magnesium concentrations in such solutions are a problem owing to the increasing tendency to crystallization of the magnesium compound present. Accordingly, an aqueous solution which is storage-stable over a relatively long period cannot be obtained having a high magnesium compound content.

The technical object of the present invention is therefore to provide a magnesium ion-containing solution which is storage stable over a long period, in particular which has a high magnesium concentration and does not exhibit unwanted crystallization of the magnesium compound or other components used.

This object is achieved by providing the embodiments characterized in the claims.

According to the present invention, an aqueous composition is provided comprising a magnesium compound, selected from a magnesium salt or a magnesium complex compound, and L-carnitine, said composition comprising at least 20% by weight of said magnesium compound and at least 5% by weight of L-carnitine.

The magnesium salts or magnesium complex compounds which are suitable in the present invention are subject in principle to no critical restriction, provided that they are sufficiently readily water-soluble. In addition, the magnesium salts and magnesium complex compounds must have good bioavailability and expedient release behaviour in human and animal organisms. Such readily water-soluble magnesium salts and magnesium complex compounds are known to those skilled in the art in the relevant subject area. For example, a magnesium complex of an amino acid, such as a magnesium complex of glutamic acid or of aspartic acid, or mixtures thereof, can be used as magnesium complex compound. It is particularly preferred to use magnesium aspartate hydrochloride, in particular magnesium L-aspartate hydrochloride, as magnesium complex compound.

According to one embodiment of the present invention, the aqueous or gel-like composition preferably comprises 40% by weight to 75% by weight, more preferably 50% by weight to 75% by weight, even more preferably 50% by weight to 70% by weight of said magnesium compound selected from a magnesium salt or a magnesium complex compound, and at least 5% by weight of L-carnitine.

L-carnitine or 3-hydroxy-4-(trimethylammonio)butyrobetaine is a colourless readily water-soluble hygroscopic substance which is a characteristic component of striped muscle and especially in fatty acid metabolism acts as carrier for acyl groups through the mitochondrial membrane.

The composition of the invention contains L-carnitine, since by addition of L-carnitine the crystallization of magnesium salts or magnesium complex compounds even in highly concentrated solutions can be effectively prevented or at least significantly delayed. Particularly preferably, the content of L-carnitine, based on the total composition, is in a range from about 5 to about 35% by weight, a range from 7 to 30% by weight being most preferred.

Surprisingly, it has been found that even at a very low concentration of L-carnitine in the aqueous solution of the invention, the problematic crystallization of a magnesium salt and/or of a magnesium complex compound can be effectively prevented or at least significantly delayed. For example it is possible to obtain a stable aqueous solution containing 70% by weight magnesium aspartate hydrochloride when 5% by weight of L-carnitine are present in the solution. The crystallization-inhibiting effect may even be increased further when the present solution contains 15% by weight of L-carnitine.

The content of the magnesium compound selected from a magnesium salt or a magnesium complex compound, based on the total composition, is preferably at least 50% by weight, storage-stable aqueous solutions also being obtained at ≧60% by weight and even ≧70% by weight, which show no, or a greatly delayed, crystallization tendency, in particular when ≧5% by weight, preferably ≧7% by weight, L-carnitine is present. Particularly preferably, the content of the magnesium compound selected from a magnesium salt or a magnesium complex compound, based on the total composition, is in a range from 50 to 75% by weight, a content in a range from 50 to 70% by weight being most preferred.

In the context of the present invention it has been found that it is even possible to obtain a stable gel-like aqueous solution which has an L-carnitine content of up to about 60% by weight, the content of the magnesium salt and/or the magnesium complex compound then being at least 20% by weight, preferably being at least 25% by weight. According to a further embodiment, the aqueous composition of the invention preferably contains at least 20% by weight of a magnesium compound selected from a magnesium salt or a magnesium complex compound, and L-carnitine in a range of 15% by weight up to 60% by weight. According to this embodiment, the content of L-carnitine is particularly preferably at least 20% by weight.

In this context, it has extremely surprisingly been found that in 100 g of an aqueous solution which contains 51% by weight magnesium aspartate hydrochloride up to 150 g of L-carnitine can be dissolved (at 20° C.), which is equivalent to a total solids content of greater than 80% by weight. This is unexpected, in particular, since the maximum solubility of L-carnitine in 100 g of water (at 20° C.) is 250 g, so that in the above-described solution, at an amount of water of about 49 g, a maximum solubility of about 121 g of L-carnitine would have been expected. This applies, furthermore, without taking into account the amount of water which is required for dissolving magnesium aspartate hydrochloride.

Without wishing to be bound thereto, one attempt at an explanation for these surprising results could be complex formation between the magnesium ions present in the solution and the L-carnitine used.

In addition, it has surprisingly been found that the density of a magnesium-containing aqueous solution decreases significantly on addition of L-carnitine. For example, the density of a sample solution of 25 ml (of 51.2% by weight magnesium L-aspartate hydrochloride, 0.1% by weight potassium sorbate and 48.7% by weight water) decreases on addition of 10 g of L-carnitine from 1.30 g/cm$^3$ to 1.26 g/cm$^3$. This could confirm the formation of a novel magnesium complex compound with L-carnitine as ligand.

The aqueous composition of the invention can in addition contain customary auxiliaries, such as stabilizers, aroma substances, preservatives, medicaments or dyes. According to a preferred embodiment, the aqueous composition of the invention contains potassium sorbate, a content of about 0.05 to 0.2% by weight potassium sorbate being particularly preferred.

The aqueous composition of the invention can be produced by simple mixing of water, a magnesium compound selected from a magnesium salt or a magnesium complex compound, L-carnitine and, if appropriate, one or more auxiliaries. However, it is preferred to produce the aqueous composition of the invention by dissolving L-carnitine in a previously formed solution of water, a magnesium salt or a magnesium complex compound and, if appropriate, one or more auxiliaries.

In addition, the aqueous or gel-like composition according to the present invention can also be converted into a corresponding spray-dried product which is obtained by spray drying an aqueous composition according to the present invention.

Furthermore, according to the present invention, the use is provided of the above-described aqueous composition or of the above-described spray-dried product in the human sector as medicament or as food supplement, or in the veterinary sector as animal feed additive, in particular for horses, poultry, pigeons, pigs, cattle, sheep and camels.

The aqueous composition of the invention is particularly suitable for administration to horses or camels via an oral syringe. By using the aqueous composition of the invention, the unwanted blocking of the piston in an oral syringe due to crystallization of the magnesium compound present can be effectively prevented.

The L-carnitine used in the composition of the invention therefore not only exhibits the surprising effect of crystallization inhibition or stabilization of the aqueous solution, but offers further advantageous properties in its property of supporting metabolism, in particular in muscle tissue, and in muscle structure and increasing stamina in humans and animals, in use of the composition of the invention as medicament, food supplement or as animal feed additive.

The examples hereinafter are reported to describe the present invention further without restricting it thereto.

EXAMPLES

Example 1 (in Particular as Veterinary Product)

A storage-stable aqueous gel which exhibited no crystallization tendency on storage over a plurality of weeks at 20° C. was obtained when the following components were mixed:
43.35 g of magnesium L-aspartate hydrochloride
0.05 g of potassium sorbate
30.24 g of water
26.36 g of L-carnitine Example 2 (in Particular as Veterinary Product)

A storage-stable aqueous gel which exhibited no crystallization tendency on storage over a plurality of weeks at 20° C. was obtained when the following components were mixed:
49.84 g of magnesium L-aspartate hydrochloride
0.05 g of potassium sorbate
20.00 g of water
30.10 g of L-carnitine Example 3 (in Particular as Veterinary Product)

A Storage-Stable Aqueous Solution Which Exhibited No crystallization tendency on storage over a plurality of weeks at 20° C. was obtained when the following components were mixed:
28.13 g of magnesium L-aspartate hydrochloride
0.029 g of potassium sorbate
54.86 g of water
16.99 g of L-carnitine Example 4 (in Particular as Human Product)

A storage-stable aqueous gel which exhibited no crystallization tendency on storage over a plurality of weeks at 20° C. was obtained when the following components were mixed:
60.51 g of magnesium L-aspartate hydrochloride
0.07 g of potassium sorbate
29.93 g of water
9.49 g of L-carnitine Example 5 (in Particular as Human Product)

A storage-stable aqueous solution which exhibited no crystallization tendency on storage over a plurality of weeks at 20° C. was obtained when the following components were mixed:
43.22 g of magnesium L-aspartate hydrochloride
0.07 g of potassium sorbate
49.93 g of water
6.78 g of L-carnitine Example 6

A storage-stable aqueous gel-like solution which exhibited no crystallization tendency on storage over a plurality of weeks at 20° C. was obtained when the following components were mixed:
51.2 g of magnesium L-aspartate hydrochloride
0.1 g of potassium sorbate
48.7 g of water
100 g of L-carnitine Example 7

A storage-stable aqueous gel-like solution which exhibited no crystallization tendency on storage over a plurality of weeks at 20° C. was obtained when the following components were mixed:
51.2 g of magnesium L-aspartate hydrochloride
0.1 g of potassium sorbate
48.7 g of water
150 g of L-carnitine Comparative Example 1

A non storage-stable aqueous gel-like solution which, after a few days, exhibited a crystalline deposit of magnesium L-aspartate hydrochloride was obtained when the following components were mixed:
70 g of magnesium L-aspartate hydrochloride
0.1 g of potassium sorbate
30 g of water

The invention claimed is:

1. An aqueous or gel-like composition comprising a magnesium complex compound which is magnesium L-aspartate hydrochloride complex compound in an amount in the range of 50% by weight to 75% by weight, and L-carnitine in an amount of at least 5% by weight.

2. The aqueous composition according to claim 1 wherein the composition is a storage-stable aqueous gel.

3. The aqueous composition according to claim 1 wherein the composition is a storage-stable aqueous solution.

4. The aqueous composition according to claim 1, further comprising one or more auxiliaries.

5. The aqueous composition according to claim 1, wherein the L-carnitine is present in an amount ranging from 5% by weight to 35% by weight.

6. The aqueous composition according to claim 5, further comprising one or more auxiliaries.

7. A method of treating a human or an animal, comprising administering to the human or animal the aqueous composition according to claim 1 as a food supplement, as an animal food additive or as a medicament.

8. A method of treating a human or an animal, comprising administering to the human or animal the aqueous composition according to claim 4 as a food supplement, as an animal food additive or as a medicament.

9. A method of treating a human or an animal, comprising administering to the human or animal the aqueous composition according to claim 5 as a food supplement, as an animal food additive or as a medicament.

10. A method of treating a human or an animal, comprising administering to the human or animal the aqueous composition according to claim 6 as a food supplement, as an animal food additive or as a medicament.

* * * * *